US011664107B2

(12) United States Patent
Saint et al.

(10) Patent No.: US 11,664,107 B2
(45) Date of Patent: May 30, 2023

(54) INTELLIGENT MEDICATION DELIVERY SYSTEMS AND METHODS USING A PRESCRIPTION-REGULATED SOFTWARE APPLICATION

(71) Applicant: MEDTRONIC MINIMED, INC., Northridge, CA (US)

(72) Inventors: Sean Saint, San Diego, CA (US); Jasper Benke, San Diego, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 999 days.

(21) Appl. No.: 16/405,837

(22) Filed: May 7, 2019

(65) Prior Publication Data
US 2019/0348165 A1    Nov. 14, 2019

Related U.S. Application Data

(60) Provisional application No. 62/668,715, filed on May 8, 2018.

(51) Int. Cl.
*G16H 20/17* (2018.01)
*A61B 5/145* (2006.01)
(Continued)

(52) U.S. Cl.
CPC ......... *G16H 20/17* (2018.01); *A61B 5/14532* (2013.01); *A61M 5/1723* (2013.01); *A61M 5/20* (2013.01); *A61M 2205/52* (2013.01)

(58) Field of Classification Search
CPC ............... G16H 20/17; A61B 5/14532; A61M 2205/52; A61M 5/1723; A61M 5/20
See application file for complete search history.

(56) References Cited

U.S. PATENT DOCUMENTS

| 4,498,904 A | 2/1985 | Turner et al. |
| 4,515,584 A | 5/1985 | Abe et al. |
| (Continued) | | |

FOREIGN PATENT DOCUMENTS

| EP | 0298067 | 4/1989 |
| EP | 513128 | 11/1992 |
| (Continued) | | |

OTHER PUBLICATIONS

Shao et al., Smartphone-controlled optogenetically engineered cells enable semiautomatic glucose homeostasis in diabetic mice, 9 Science Translational Medicine 1-13 (Apr. 26, 2017) (Year: 2017).*

(Continued)

*Primary Examiner* — Evangeline Barr
*Assistant Examiner* — Jordan L Jackson
(74) *Attorney, Agent, or Firm* — Carter, DeLuca & Farrell LLP

(57) ABSTRACT

Systems, devices and methods are disclosed for a prescription-regulated software application and an associated medical device. In some aspects, a smart medicine-injection device (e.g., smart insulin pen) is configured to be in communication with a patient's companion device (e.g., smartphone) having a software application (prescription app) that serves the patient as a complimentary medical device to the smart medicine-injection device, in which only certain features and functionalities of the prescription app are fully operable based on device pairing with the smart medicine-injection device to unlock medical device capabilities only available to the patient through prescription.

20 Claims, 5 Drawing Sheets

(51) Int. Cl.
*A61M 5/172* (2006.01)
*A61M 5/20* (2006.01)

(56) References Cited

U.S. PATENT DOCUMENTS

| | | |
|---|---|---|
| 4,950,216 A | 8/1990 | Weder |
| 4,973,318 A | 11/1990 | Holm et al. |
| 4,988,660 A | 1/1991 | Campbell |
| 5,279,586 A | 1/1994 | Balkwill |
| 5,626,566 A | 5/1997 | Petersen et al. |
| 5,681,285 A | 10/1997 | Ford et al. |
| 5,822,715 A | 10/1998 | Worthington et al. |
| 5,925,021 A | 7/1999 | Castellano et al. |
| 5,984,900 A | 11/1999 | Mikkelsen |
| 6,004,297 A | 12/1999 | Steenfeldt-Jensen et al. |
| 6,042,571 A | 3/2000 | Hjertman et al. |
| 6,235,004 B1 | 5/2001 | Steenfeldt-Jensen et al. |
| 6,302,855 B1 | 10/2001 | Lav et al. |
| 6,482,185 B1 | 11/2002 | Hartmann |
| 6,817,986 B2 | 11/2004 | Slate et al. |
| 7,591,801 B2 | 9/2009 | Brauker et al. |
| 7,905,833 B2 | 3/2011 | Brister et al. |
| 7,955,303 B2 | 6/2011 | Burren et al. |
| 7,976,492 B2 | 7/2011 | Brauker et al. |
| 8,221,356 B2 | 7/2012 | Enggaard et al. |
| 8,229,535 B2 | 7/2012 | Mensinger et al. |
| 8,231,531 B2 | 7/2012 | Brister et al. |
| RE43,834 E | 11/2012 | Steenfeldt-Jensen et al. |
| 8,460,231 B2 | 6/2013 | Brauker et al. |
| 8,565,848 B2 | 10/2013 | Brister et al. |
| D694,252 S | 11/2013 | Helm |
| 8,591,455 B2 | 11/2013 | Mensinger et al. |
| 8,663,109 B2 | 3/2014 | Brister et al. |
| 8,721,585 B2 | 5/2014 | Mensinger et al. |
| 8,750,955 B2 | 6/2014 | Mensinger et al. |
| 8,808,228 B2 | 8/2014 | Brister et al. |
| 8,882,741 B2 | 11/2014 | Brauker et al. |
| 8,920,401 B2 | 12/2014 | Brauker et al. |
| 8,926,585 B2 | 1/2015 | Brauker et al. |
| D727,928 S | 4/2015 | Allison et al. |
| 9,020,572 B2 | 4/2015 | Mensinger et al. |
| 9,050,413 B2 | 6/2015 | Brauker et al. |
| D738,385 S | 9/2015 | Lim et al. |
| 9,143,569 B2 | 9/2015 | Mensinger et al. |
| 9,155,843 B2 | 10/2015 | Brauker et al. |
| D747,333 S | 1/2016 | Supino et al. |
| D748,101 S | 1/2016 | Bang et al. |
| D748,126 S | 1/2016 | Sarukkai et al. |
| D749,103 S | 2/2016 | Song |
| D753,685 S | 4/2016 | Zimmerman et al. |
| D754,689 S | 4/2016 | Lee |
| D759,684 S | 6/2016 | Bijlani et al. |
| D761,280 S | 7/2016 | Chung et al. |
| D763,308 S | 8/2016 | Wang et al. |
| D766,958 S | 9/2016 | Salazar Cardozo et al. |
| 9,446,194 B2 | 9/2016 | Kamath et al. |
| D777,760 S | 1/2017 | Zhao et al. |
| D781,890 S | 3/2017 | Gathman et al. |
| D783,037 S | 4/2017 | Hariharan et al. |
| D783,648 S | 4/2017 | Vazquez et al. |
| D784,391 S | 4/2017 | Yuguchi et al. |
| D785,025 S | 4/2017 | Zimmerman et al. |
| D786,273 S | 5/2017 | Herman et al. |
| 9,672,328 B2 | 6/2017 | Saint |
| D791,806 S | 7/2017 | Brewington et al. |
| D794,047 S | 8/2017 | Gandhi et al. |
| D795,900 S | 8/2017 | Bischoff et al. |
| D795,919 S | 8/2017 | Bischoff et al. |
| D795,927 S | 8/2017 | Bischoff et al. |
| D797,760 S | 9/2017 | Tsujimura et al. |
| D798,312 S | 9/2017 | Tsujimura et al. |
| 9,775,543 B2 | 10/2017 | Brister et al. |
| D808,986 S | 1/2018 | Dudey |
| D809,544 S | 2/2018 | Ambielli |
| D809,545 S | 2/2018 | Ban et al. |
| D811,425 S | 2/2018 | Olsen et al. |
| D815,127 S | 4/2018 | Phillips et al. |
| D815,667 S | 4/2018 | Yeung |
| 9,937,293 B2 | 4/2018 | Brauker et al. |
| D819,043 S | 5/2018 | Yamaura et al. |
| D820,297 S | 6/2018 | Gardner et al. |
| 9,996,668 B2 | 6/2018 | Reihman et al. |
| D831,049 S | 10/2018 | Agarwal et al. |
| D831,684 S | 10/2018 | Ghosh |
| D832,292 S | 10/2018 | Hu et al. |
| D832,870 S | 11/2018 | Hu |
| D833,469 S | 11/2018 | Coleman et al. |
| D835,118 S | 12/2018 | Lee et al. |
| D837,807 S | 1/2019 | Baber et al. |
| D838,734 S | 1/2019 | Kruse et al. |
| 10,169,539 B2 | 1/2019 | Reihman et al. |
| D842,888 S | 3/2019 | Krainer et al. |
| D843,402 S | 3/2019 | Casse et al. |
| D846,590 S | 4/2019 | Cabrera et al. |
| D847,165 S | 4/2019 | Cheney et al. |
| D849,757 S | 5/2019 | Jing et al. |
| 10,278,580 B2 | 5/2019 | Brister et al. |
| 2003/0065536 A1 | 4/2003 | Hansen et al. |
| 2004/0039255 A1 | 2/2004 | Simonsen et al. |
| 2005/0038674 A1 | 2/2005 | Braig et al. |
| 2005/0049179 A1 | 3/2005 | Davidson et al. |
| 2005/0182358 A1 | 8/2005 | Veit et al. |
| 2005/0192494 A1 | 9/2005 | Ginsberg |
| 2005/0192557 A1 | 9/2005 | Brauker et al. |
| 2006/0036144 A1 | 2/2006 | Brister et al. |
| 2006/0173417 A1 | 8/2006 | Rosen et al. |
| 2007/0021715 A1 | 1/2007 | Kohlbrenner et al. |
| 2007/0038044 A1 | 2/2007 | Dobbles et al. |
| 2007/0173708 A9 | 7/2007 | Dobbles et al. |
| 2007/0186923 A1 | 8/2007 | Poutiatine et al. |
| 2007/0239486 A1 | 10/2007 | Gordon |
| 2008/0162192 A1 | 7/2008 | Vonk et al. |
| 2008/0188813 A1 | 8/2008 | Miller et al. |
| 2008/0201169 A1 | 8/2008 | Galasso et al. |
| 2008/0234663 A1 | 9/2008 | Yodat et al. |
| 2008/0235053 A1 | 9/2008 | Ray et al. |
| 2008/0262469 A1 | 10/2008 | Brister et al. |
| 2009/0036771 A1 | 2/2009 | Fago et al. |
| 2009/0048561 A1 | 2/2009 | Burren et al. |
| 2009/0069742 A1 | 3/2009 | Larsen |
| 2009/0131875 A1 | 5/2009 | Green |
| 2009/0163793 A1 | 6/2009 | Koehler |
| 2009/0209938 A1 | 8/2009 | Aalto-Setala |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0299276 A1 | 12/2009 | Brauker et al. |
| 2010/0049126 A1 | 2/2010 | Bronfeld et al. |
| 2010/0063438 A1 | 3/2010 | Bengtsson |
| 2010/0081993 A1 | 4/2010 | O'Connor |
| 2010/0185075 A1 | 7/2010 | Brister et al. |
| 2010/0261987 A1 | 10/2010 | Kamath et al. |
| 2010/0331656 A1 | 12/2010 | Mensinger et al. |
| 2010/0331657 A1 | 12/2010 | Mensinger et al. |
| 2011/0009727 A1 | 1/2011 | Mensinger et al. |
| 2011/0196306 A1* | 8/2011 | De La Huerga .. A61M 5/16827 604/93.01 |
| 2011/0264033 A1 | 10/2011 | Jensen et al. |
| 2011/0270158 A1 | 11/2011 | Brauker et al. |
| 2011/0275410 A1* | 11/2011 | Caffey ............. A61M 5/14526 604/151 |
| 2011/0275986 A1 | 11/2011 | Bashan |
| 2011/0281791 A1 | 11/2011 | Zion et al. |
| 2011/0313349 A1 | 12/2011 | Krulevitch et al. |
| 2011/0313350 A1 | 12/2011 | Krulevitch et al. |
| 2011/0313395 A1 | 12/2011 | Krulevitch et al. |
| 2012/0072236 A1 | 3/2012 | Atkin |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0215201 A1 | 8/2012 | Brauker et al. |
| 2012/0220979 A1 | 8/2012 | Brauker et al. |

(56) References Cited

U.S. PATENT DOCUMENTS

| | | | |
|---|---|---|---|
| 2012/0238851 A1* | 9/2012 | Kamen | A61M 5/14244 604/151 |
| 2012/0238852 A1 | 9/2012 | Brauker et al. | |
| 2012/0296311 A1 | 11/2012 | Brauker et al. | |
| 2013/0035575 A1 | 2/2013 | Mayou et al. | |
| 2013/0035865 A1 | 2/2013 | Mayou et al. | |
| 2013/0035871 A1 | 2/2013 | Mayou et al. | |
| 2013/0171938 A1 | 7/2013 | Mears et al. | |
| 2013/0184996 A1 | 7/2013 | Zivitz et al. | |
| 2013/0197445 A1 | 8/2013 | Schabbach et al. | |
| 2013/0197479 A1 | 8/2013 | Butler et al. | |
| 2013/0211248 A1 | 8/2013 | Cowan et al. | |
| 2013/0291116 A1 | 10/2013 | Homer | |
| 2014/0012117 A1 | 1/2014 | Mensinger et al. | |
| 2014/0012118 A1 | 1/2014 | Mensinger et al. | |
| 2014/0012510 A1 | 1/2014 | Mensinger et al. | |
| 2014/0012511 A1 | 1/2014 | Mensinger et al. | |
| 2014/0074041 A1 | 3/2014 | Pedersen et al. | |
| 2014/0113856 A1 | 4/2014 | Pohl et al. | |
| 2014/0114158 A1 | 4/2014 | Brister et al. | |
| 2014/0114161 A1 | 4/2014 | Kamath et al. | |
| 2014/0257065 A1 | 9/2014 | Walsh | |
| 2014/0276531 A1 | 9/2014 | Walsh | |
| 2014/0288494 A1 | 9/2014 | Brister et al. | |
| 2014/0325065 A1* | 10/2014 | Birtwhistle | H04L 47/70 709/225 |
| 2015/0065047 A1* | 3/2015 | Wu | H04W 4/80 455/41.2 |
| 2015/0073337 A1 | 3/2015 | Saint et al. | |
| 2015/0202377 A1 | 7/2015 | Haupt | |
| 2015/0351683 A1 | 12/2015 | Brauker et al. | |
| 2015/0359965 A1 | 12/2015 | O'Connor et al. | |
| 2016/0012205 A1* | 1/2016 | Saint | A61M 5/31528 604/189 |
| 2016/0030683 A1 | 2/2016 | Taylor | |
| 2016/0066843 A1 | 3/2016 | Mensinger et al. | |
| 2016/0081632 A1 | 3/2016 | Kamath et al. | |
| 2016/0101232 A1 | 4/2016 | Kamath et al. | |
| 2017/0068799 A1 | 3/2017 | Mensinger et al. | |
| 2017/0124272 A1 | 5/2017 | Reihman et al. | |
| 2017/0124275 A1 | 5/2017 | Reihman et al. | |
| 2017/0124284 A1* | 5/2017 | McCullough | A61M 5/20 |
| 2017/0124350 A1 | 5/2017 | Reihman et al. | |
| 2017/0131993 A1 | 5/2017 | Salameh et al. | |
| 2017/0132120 A1 | 5/2017 | Salameh et al. | |
| 2017/0185283 A1 | 6/2017 | Bhavaraju et al. | |
| 2017/0185284 A1 | 6/2017 | Bhavaraju et al. | |
| 2017/0189625 A1 | 7/2017 | Cirillo et al. | |
| 2017/0270276 A1 | 9/2017 | Saint et al. | |
| 2017/0286194 A1 | 10/2017 | Morris et al. | |
| 2017/0286614 A1 | 10/2017 | Morris et al. | |
| 2017/0304540 A1* | 10/2017 | Despa | G16H 20/10 |
| 2017/0366617 A1 | 12/2017 | Mensinger et al. | |
| 2017/0367627 A1 | 12/2017 | Brister et al. | |
| 2018/0185587 A1 | 7/2018 | Brauker et al. | |
| 2018/0303417 A1 | 10/2018 | Mensinger et al. | |
| 2018/0353698 A1 | 12/2018 | Saint et al. | |
| 2019/0015020 A1 | 1/2019 | Brister et al. | |
| 2019/0035500 A1 | 1/2019 | Saint et al. | |
| 2019/0132801 A1 | 5/2019 | Kamath et al. | |
| 2019/0173885 A1 | 6/2019 | Kamath et al. | |
| 2019/0125224 A1 | 8/2019 | Kamath et al. | |

FOREIGN PATENT DOCUMENTS

| | | | |
|---|---|---|---|
| EP | 927057 | 7/1999 | |
| EP | 2572740 | 3/2013 | |
| EP | 3053279 B1 * | 4/2021 | A61B 5/0002 |
| WO | 9638190 | 12/1996 | |
| WO | 2010052275 | 5/2010 | |
| WO | 2011041007 | 4/2011 | |
| WO | 2012046199 | 4/2012 | |
| WO | 2013053695 | 4/2013 | |
| WO | 2014128157 | 8/2014 | |
| WO | 2015047870 | 4/2015 | |
| WO | 2015169814 | 11/2015 | |
| WO | 2015185686 | 12/2015 | |
| WO | 2016071912 | 5/2016 | |
| WO | 2017132577 | 3/2018 | |

OTHER PUBLICATIONS

Cision PR News Wire, "CompaNion Medical Announces Insights by InPen, the Future of MDI Reports", Jun. 20, 2018.

Copenheaver, B. R., Authorized Officer, ISA/US, International Search Report and Written Opinion, International Application No. PCT/US2014/056336, dated Dec. 31, 2014, 10 pages.

Young, Lee W., ISA/US, International Search Report, International Application No. PCT/US15/40069, dated Dec. 22, 2015, 13 pages.

Young, Lee W., ISA/US, Invitation to Pay Additional Fees and Partial Search Report, International Application No. PCT/US15/40069, dated Oct. 1, 2015, 2 pages.

Extended European Search Report for European Patent Application No. 14849422.2, dated May 4, 2017, 11 pages.

International Search Report and Written Opinion for PCT Application No. PCT/US2018/036768; dated Aug. 31, 2018, 10 pages.

International Search Report and Written Opinion for PCT Application No. PCT/US2017/15452, dated May 23, 2017, 14 pages.

Extended European Search Report for European Patent Application No. 17745019.4, dated Aug. 6, 2019, 9 pages.

International Search Report and Written Opinion for PCT Application No. PCT/US2018/55646, dated Feb. 6, 2019, 15 pages.

* cited by examiner

370

371

Determining a medically-prescribed hardware device is within a communication range of a mobile device to allow wireless communications between the medically-prescribed hardware device and the mobile device

373

Storing a code in a memory of the medically-prescribed injection device

375

Transmitting a wireless transmission including the code by the medically-prescribed injection device to the mobile device

377

Receiving a subsequent wireless transmission from the mobile device that includes an instruction to carry out a medically-regulated operation of the medically-prescribed injection device, where the instruction is transmitted by the mobile device as a result of validation of the code to authorize unlocking of one or more features of the medically-regulated software application on the mobile device

FIG. 3C

INTELLIGENT MEDICATION DELIVERY SYSTEMS AND METHODS USING A PRESCRIPTION-REGULATED SOFTWARE APPLICATION

CROSS-REFERENCE TO RELATED APPLICATIONS

This patent document claims priorities to and benefits of U.S. Provisional Patent Application No. 62/668,715 entitled "INTELLIGENT MEDICATION DELIVERY SYSTEMS AND METHODS USING A PRESCRIPTION-REGULATED SOFTWARE APPLICATION" filed on May 8, 2018. The entire content of the aforementioned patent application is incorporated by reference as part of the disclosure of this patent document.

TECHNICAL FIELD

This patent document relates to medicine administering and tracking systems, devices, and processes.

BACKGROUND

Diabetes mellitus, also referred to as diabetes, is a metabolic disease associated with high blood sugar due to insufficient production or use of insulin by the body. Diabetes is widely-spread globally, affecting hundreds of millions of people, and is among the leading causes of death globally. Diabetes has been categorized into three categories or types: type 1, type 2, and gestational diabetes. Type 1 diabetes is associated with the body's failure to produce sufficient levels of insulin for cells to uptake glucose. Type 2 diabetes is associated with insulin resistance, in which cells fail to use insulin properly. The third type of diabetes is commonly referred to as gestational diabetes, which can occur during pregnancy when a pregnant woman develops a high blood glucose level. Gestational diabetes can develop into type 2 diabetes, but often resolves after the pregnancy.

SUMMARY

Systems, devices and methods are disclosed for a prescription-regulated software application and medical device.

In some aspects, a smart medicine-injection device (e.g., smart insulin pen) is configured to be in communication with a patient's companion device (e.g., smartphone) having a software application (app) that serves the patient as a complimentary medical device to the smart medicine-injection device, which the medical device app is only fully operable based on a device pairing with the smart medicine-injection device to unlock capabilities available based prescription. In some implementations, the disclosed intelligent medicine administration systems dispense and track injected doses of the medicine to the patient and provide health management capabilities for patients and caregivers.

In some aspects, a computer-implemented method for providing a medically-prescribed software application includes obtaining, at a mobile device, a software application associated with a medical device, wherein the software application includes one or more operational features that, when executed, cause the mobile to device to operate in a manner that is regulated to require a medical prescription for use of the software application; initially launching, at the mobile device, the software application, wherein the one or more operational features of the software application are inoperable by default; receiving, at the mobile device, a wireless signal from the medical device to pair the medical device to the mobile device for intermittent and/or periodic communications; and activating, at the mobile device, the one or more operational features of the software application as operable using data received during pairing of the medical device with the mobile device.

In some aspects, a computer-implemented method for enabling use of a medically-regulated software application on a mobile device with a medically-prescribed injection device includes determining that the medically-prescribed injection device is within a communication range of the mobile device so as to allow wireless communications between the medically-prescribed injection device and the mobile device; at the mobile device, launching the medically-regulated software application having one or more operational features that are inoperable by default, wherein the one or more operational features, when executed, cause the mobile to device to operate in a manner that is regulated to require a medical prescription for use of the medically-regulated software application; at the mobile device, receiving a wireless transmission from the medically-prescribed injection device; processing information associated with the wireless transmission indicative that the medically-prescribed injection device is authorized; and based on the processing unlocking the one or more features of the medically-regulated software application that are inoperable by default for use with the medically-prescribed injection device.

In some aspects, a computer-implemented method for enabling use of a medically-regulated software application for a mobile device with a medically-prescribed injection device includes determining that the medically-prescribed injection device is within a communication range of the mobile device so as to allow wireless communications between the medically-prescribed injection device and the mobile device, wherein the medically-regulated software application has one or more operational features that are inoperable by default, and wherein the one or more operational features, when executed, cause the mobile device to operate in a manner that is regulated to require a medical prescription for use of the medically-regulated software application; at the medically-prescribed injection device, storing a code in a memory of the medically-prescribed injection device; at the medically-prescribed injection device, transmitting a wireless transmission including the code to the mobile device; and at the medically-prescribed injection device, receiving a subsequent wireless transmission from the mobile device that includes an instruction to carry out a medically-regulated operation of the medically-prescribed injection device, wherein the instruction is transmitted by the mobile device as a result of a validation of the code by the mobile device to authorize unlocking the one or more operational features of the medically-regulated software application that are otherwise inoperable by default for use with the medically-prescribed injection device.

BRIEF DESCRIPTION OF THE DRAWINGS

FIGS. 3A-3C show diagrams of example embodiments of methods for activating features of a prescription-regulated software application associated with a medical device in accordance with the present technology.

DETAILED DESCRIPTION

Figure 1A:
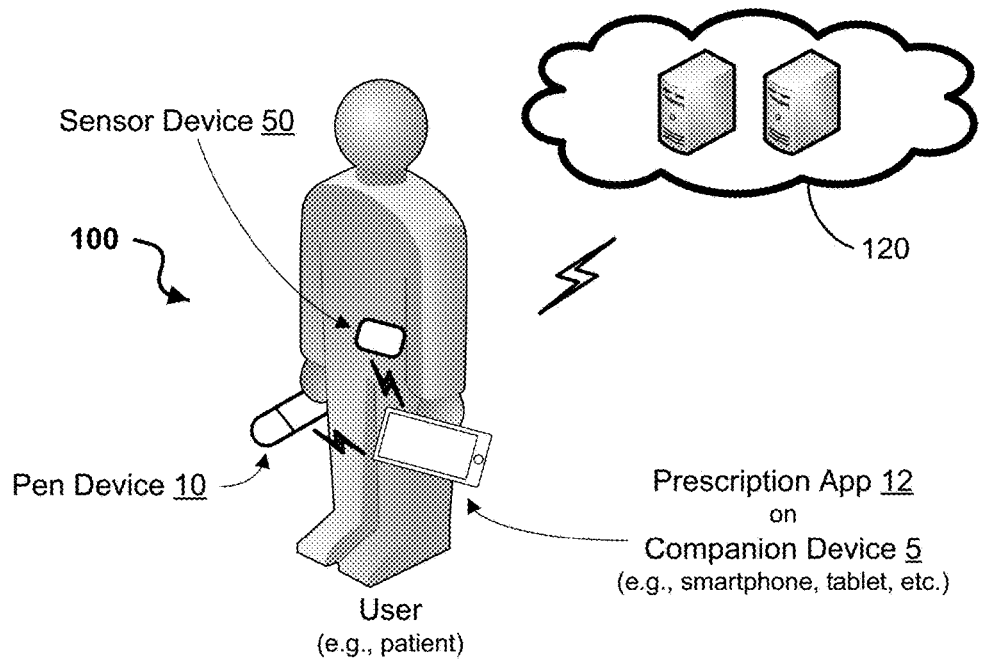
FIG. 1A shows a diagram of an example embodiment of an intelligent medicine administering system in accordance with the present technology.

Various diseases and medical conditions, such as diabetes, require a patient to self-administer doses of a fluid medication. Typically, when administering a fluid medication, the appropriate dose amount is set and dispensed by the patient using a syringe, a pen, or a pump. For example, self-administered medicaments or medicine include insulin used to treat diabetes, Follistim® used to treat infertility, or other injectable medicines such as Humira®, Enbrel®, Lovenox® and Ovidrel®, or others.

A medicament pen is a device that can be used to inject a quantity of a medicine (e.g., single or multiple boluses or doses of the medicine) into a user's body, where more than one dose can be stored in a medicine cartridge contained in the pen device. Pens offer the benefit of simplicity over other methods of delivery, such as syringe or pump-based methods. For example, syringes typically require more steps to deliver a dose, and pumps typically are more complicated to use and require a constant tether to the patient. However, previously there has not been an automated way to track and communicate the doses given with the pen in a simple, effective and reliable manner. In addition, it can be difficult to know how much to dose with the pen, when to dose, or if the patient dosed at all.

As with the dosing of any medication, it is sometimes hard for a patient to remember if a dose has been given. For this reason, for example, pill reminders have been developed where the patient places the medication for the day in a cup labeled with that day. Once they take their medication, there is no question it has been taken because the pills are no longer in the cup. Yet, there are no widely acceptable solutions that address this problem for injection-based therapies. Therefore, without simple, effective and reliable ways of tracking medicine doses, particularly for managing lifelong or chronic conditions like diabetes, patients may easily miss a dose or administer an incorrect dose (e.g., under-dose or over-dose) of their medicine which may result in serious, dangerous consequences to their health.

Some medical device systems include independent, stand-alone software applications that operate on a computing device. One example includes mobile device software applications that help the users manage their own health and wellness, including dealing with an acute or chronic disease or dysfunction and managing data associated with such uses. These types of apps have been termed "mobile medical applications" by the United States Food and Drug Administration (FDA). In 2013, the FDA issued the first regulatory guidance to outline the agency's intended oversight of mobile medical apps as medical devices, which included a greater focus on the apps that it deemed presented a greater risk to patients if they failed to work as intended or impact the functionality or performance of a traditional medical device, such as a sensor or injection device.

Recently, certain mobile medical apps have become prescription only. This means that access to and/or operation of these prescription-only apps must be controlled and only used with a prescription. Conventional prescription-based applications are downloadable from an app store, but require a code to be fully functional to the user on his/her mobile device, e.g., smartphone. In some cases, a code is required to download the prescription-based app in the first place.

Yet, the conventional approach to provide prescription software applications is dangerously flawed due to their vulnerability to hacks that can allow anyone to access and operate the prescription app. For example, several existing mobile medical apps, available through prescription only, unlock and are operable based on a single code for the app regardless of the device the app has been installed. These codes have been released online, allowing anyone to obtain the code and unlock the mobile medical app for their own use, e.g., without prescription. Moreover, some conventional approaches require the patient user to obtain the code directly from their physician, e.g., typically at an appointment, which is a burden to patient users and health care professionals because of the substantial financial and time costs required to obtain the code.

Systems, devices and methods are disclosed for a prescription-regulated software application and associated medical device, such as a medicament injection device like an injection pen, pump or wearable patch for delivering a prescription drug.

In some aspects, a smart medicine-injection device (e.g., smart insulin pen) is configured to be in communication with a patient's companion device (e.g., smartphone) having a prescription app that serves the patient as a complimentary medical device to the smart medicine-injection device, in which the prescription app is only fully operable based on a specific device pairing with the smart medicine-injection device to unlock the capabilities intended only to be utilized with a prescription.

In some embodiments, the prescription-regulated software application (also referred to as the prescription app) operates as a complimentary medical device to the medicine injection device (also referred to as the pen device), such as by provide various support tools including a dose calculator and decision support modules to calculate and recommend the dose of a medicine (e.g., insulin) the patient should administer using the wirelessly connected medicine injection device, as well as to provide control over several functionalities of the injection device, e.g., such as monitoring and recording dose sizes dialed on and/or dispensed from the injection device. For example, communication between the pen device and the companion device provides the ability for dose tracking, logging, calculating, recommending, and/or communicating dose data with a user (e.g., patient user, health care provider (HCP) and/or caregiver), and other advantages of the intelligent medicine administering system. For example, each bolus that is dispensed by the pen device can be automatically logged and communicated to the companion device.

FIG. 1A shows a diagram of an example embodiment of an intelligent medicine administering system 100 in accordance with the present technology. The system 100 includes a pen device 10 in wireless communication with a mobile computing and communication device 5 of a patient user, also referred to as the user's companion device. The pen device 10 is operable to select, set and/or dispense a dose of the medicine for dispensing. In some implementations, the companion device 5 includes a smartphone, tablet, and/or wearable computing device, such as a smartwatch, smartglasses, etc. In some implementations, the companion device 5 is in communication with other computing devices, such as a laptop and/or desktop computer, a smart television, or network-based server computer. The companion device 5 includes a prescription app 12 associated with the pen device 10 of the intelligent medicine administering system 100. In some embodiments, the system 100 includes a data processing system 120 in communication with the companion device 5 and/or the pen device 10. The data processing system 120 can include one or more computing devices in a computer system or communication network accessible via the Internet (referred to as "the cloud"), e.g., including servers and/or databases in the cloud.

The prescription-regulated app 12 is paired with the pen device 10, which may also be a prescription-only medical device. In implementations, the pairing (also referred to as bonding) of the companion device 5 to the prescription-only pen device 10 indicates to the prescription-regulated application 12 that the user has a prescription for operating the regulated and protected features of the application, which can augment performance and provide important features to the intelligent medicine administering system 100. The act of pairing (bonding) therefore enables the full functionality of the prescription app 12. For example, in some cases the pairing may enable the entire app, in which the prescription app 12 is disabled without the specialized pairing; whereas in other cases, the pairing may enable the prescription-only features of the prescription app 12, which otherwise provides some limited, nonprescription-regulated features without the specialized pairing.

In some implementations, for example, the prescription app 12 can monitor and/or control functionalities of the pen device 10 and provide a dose calculator and/or decision support modules that can calculate and recommend a dose of the medicine for the patient user to administer using the pen device 10.

The companion device 5 can be used to obtain, process and/or display contextual data that can be used to relate to the patient user's health condition, including the condition for which the pen device 10 is used to treat. In an illustrative example, the companion device 5 is operable to track the patient user's location; the patient user's physical activity including step count, movement distance and/or intensity, estimated calories burned, and/or activity duration; and/or the patient user's interaction pattern with the companion device 5. In some implementations, the app 12 can aggregate and process the contextual data to generate decision support outputs to guide and aid the patient user in using the pen device 10 and/or managing their behavior to promote better health outcomes in treating his/her health condition.

In some embodiments, for example, the system 100 can optionally include a sensor device 50 to monitor one or more health metrics of the patient user. Examples of health metric data monitored by the sensor device 50 include analytes, such as glucose, heart rate, blood pressure, user movement, or other. In some implementations, the sensor device 50 is a wearable sensor device such as a continuous glucose monitor (CGM) to obtain transcutaneous or blood glucose measurements that are processed to produce continuous glucose values. For example, the continuous glucose monitor can include a glucose processing module implemented on a stand-alone display device and/or implemented on the companion device 5, which processes, stores and displays the continuous glucose values for the patient user.

Figure 1B:
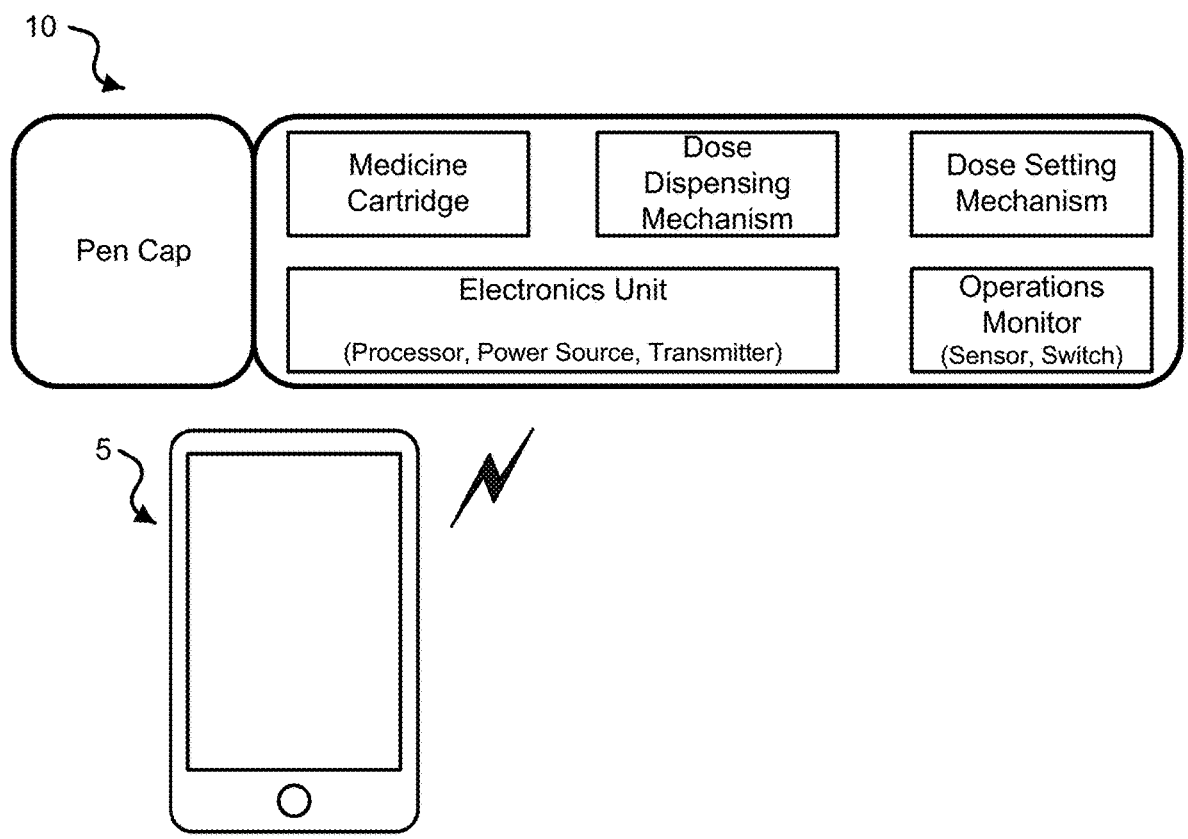
FIG. 1B shows a diagram of an example embodiment of a pen device of the intelligent medicine administering system of FIG. 1A.

FIG. 1B shows a diagram of an example embodiment of the pen device 10 of the intelligent medicine administering system 100. The pen device 10 is structured to have a body which contains the medicine cartridge (e.g., which can be replaceable). The pen device 10 is structured to include a dose dispensing mechanism to dispense (e.g., deliver) the medicine contained in the medicine cartridge out of the pen device; a dose setting mechanism to select and/or set the dose to be dispensed; an operations monitoring mechanism to determine that the pen device is being operated and/or to monitor the operation of the dose being dispensed (e.g., such as a switch and/or sensor, or an encoder); and an electronics unit that can include a processor, a memory, a battery or other power source, and a transmitter.

The pen device 10 is configured in communication with the patient user's mobile computing and communication device 5, e.g., such as the user's smartphone, tablet, and/or wearable computing device, such as a smartwatch, smartglasses, etc. and/or a user's laptop and/or desktop computer, a smart television, or network-based server computer.

In some implementations of the system 100, for example, to use the pen device 10, the user first dials up a dose using a dose knob. The dose knob of the pen device 10 can be included as part of the dose setting mechanism and/or the dose dispensing mechanism. For example, the dose may be adjusted up or down prior to administration of the dose. When the user applies a force against a dose dispensing button (e.g., presses against the dose dispensing button that is caused to protrude outward from the pen's body upon dialing the dose using the dose knob), a pushing component (e.g., also referred to as a 'plunger') of the dose dispensing mechanism is depressed against an abutment of the medicine cartridge loaded in the pen device 10 to cause the pen device 10 to begin to dispense the medicine, in which the quantity dispensed is in accordance with that set by the dose setting mechanism. In such implementations, the operations monitoring mechanism of the pen device 10 will begin to sense movement of a rotating component or shaft that drives the plunger, for example, in which the movement is sensed through an encoder. In some examples, the encoder can be configured to sense the rotation of a component that is coupled to the drive shaft, and as the drive shaft rotates the plunger moves linearly; and therefore, by sensing rotation of the component, the movement of the drive shaft and the plunger is sensed. Movement of the encoder may be detected as data processed by a processor of the electronics unit of the pen device 10, which can be used to measure the dose. In some implementations, the processor can then store the size of the dose along with a time stamp for that dose. In some implementations, the pen device 10 can then transmit the dose and related information to the companion device 5. In such implementations when the dose is transmitted, the data associated with the particular transmitted dose is marked in the memory of the pen device 10 as transmitted. In such implementations if the dose was not yet transmitted to the companion device 5, then the data associated with the dose will be transmitted at the next time a successful communication link between the pen device 10 and the companion device 5 is established.

The operations monitoring mechanism of the pen device 10 can include a sensor that can utilize any method of sensing rotary or linear movement. Non-limiting examples of such sensors include rotary and linear encoders, Hall effect and other magnetic based sensors, linearly variable displacement transducers, or any other appropriate method of sensing known in the art.

The dose dispensing mechanism of the pen device 10 can include a manually powered mechanism or a motorized mechanism. In either case, a force (e.g., either produced by the patient or by an electrically-powered motor) pushes on the plunger of the dose dispensing mechanism to in turn force a receiving plunger of the medicament vial or cartridge to deliver the specific amount of the medicament. In some implementations, for example, the dose dispensing mechanism can be adjusted to deliver the dose over a different period of time. In one example, the dose dispensing mechanism can be operated such that the plunger is pushed in by an adjustable tension spring or change the speed of the motor to inject the dose over a time frame (e.g., 1 s, 5 s or other) to aid in reducing the pain of dosing. In one example, the dose dispensing mechanism can be operated over a much longer period of time, e.g., to better match the dynamics of carbohydrates, which can be like an extended bolus with a pump.

The prescription app 12 of the companion device 5 associated with the pen device 10 provides a user interface to allow the user to manage his/her health-related data. In some implementations, for example, the prescription app 12 can be configured to control some functionalities of the pen device 10. In some implementations, for example, the prescription app 12 provides an interactive user interface to allow a user to manage settings of the pen device 10, and settings for the companion device 5 (e.g., smartphone, tablet, or wearable computing device) that can affect the functionality of the system 100. In implementations, for example, the companion device 5 is an independent portable device that the user may carry on his/her person. In example embodiments of the independent portable companion device 5, the companion device 5 includes a data processing unit, wireless communication unit to allow the device to communicate with the pen device 10, and a display unit.

Figure 1C:
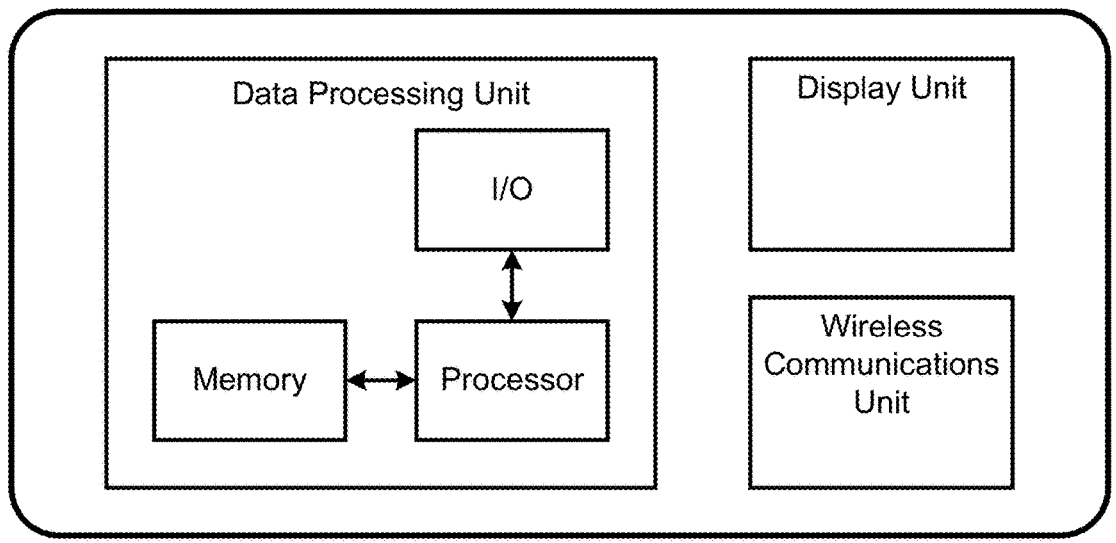
FIG. 1C shows a block diagram of an example embodiment of the companion device of the intelligent medicine administering system of FIG. 1A.

FIG. 1C shows a block diagram of an example embodiment of the companion device 5 of the intelligent medicine administering system 100. The data processing unit of the companion device 5 includes a processor to process data, a memory in communication with the processor to store data, and an input/output unit (I/O) to interface the processor and/or memory to other modules, units or devices of the companion device 5 or external devices. For example, the processor can include a central processing unit (CPU) or a microcontroller unit (MCU). For example, the memory can include and store processor-executable code, which when executed by the processor, configures the data processing unit to perform various operations, e.g., such as receiving information, commands, and/or data, processing information and data, and transmitting or providing information/data to another device. In some implementations, the data processing unit can transmit raw or processed data to a computer system or communication network accessible via the Internet (referred to as 'the cloud') that includes one or more remote computational processing devices (e.g., servers in the cloud). To support various functions of the data processing unit, the memory can store information and data, such as instructions, software, values, images, and other data processed or referenced by the processor. For example, various types of Random Access Memory (RAM) devices, Read Only Memory (ROM) devices, Flash Memory devices, and other suitable storage media can be used to implement storage functions of the memory unit. The I/O of the data processing unit can interface the data processing unit with the wireless communications unit to utilize various types of wired or wireless interfaces compatible with typical data communication standards, for example, which can be used in communications of the data processing unit with other devices such as the pen device 10, via a wireless transmitter/receiver (Tx/Rx) unit, e.g., including, but not limited to, Bluetooth, Bluetooth low energy, Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, NFC (Near Field Communication), and parallel interfaces. The I/O of the data processing unit can also interface with other external interfaces, sources of data storage, and/or visual or audio display devices, etc. to retrieve and transfer data and information that can be processed by the processor, stored in the memory unit, or exhibited on an output unit of the companion device 5 or an external device. For example, a display unit of the companion device 5 can be configured to be in data communication with the data processing unit, e.g., via the I/O, to provide a visual display, an audio display, and/or other sensory display that produces the user interface of the prescription application 12. In some examples, the display unit can include various types of screen displays, speakers, or printing interfaces, e.g., including but not limited to, light emitting diode (LED), or liquid crystal display (LCD) monitor or screen, cathode ray tube (CRT) as a visual display; audio signal transducer apparatuses as an audio display; and/or toner, liquid inkjet, solid ink, dye sublimation, inkless (e.g., such as thermal or UV) printing apparatuses, etc.

In operations of the intelligent medicine administering system 100, for example, when a dosing event (e.g., an amount of fluid is dispensed from the pen device 10), a time stamp associated with the dispensing is referenced is recorded by the processing unit of the pen device 10 (e.g., stored in the memory of the pen device 10). For example, the time stamp may be the current time or a time where a count-up timer is used. When the dose information is eventually transmitted to the prescription app 12 of the companion device 5, the time stamp and/or a 'time-since-dose' parameter is transmitted by the pen device 10 and received by the companion device 5 and stored in the memory of the data processing unit of the companion device 5. In some implementations, for example, the time of the dose can be determined without the pen having to know the current time. This can simplify operation and setup of the pen device 10. In some implementations, for example, a user time is initialized on the pen device 10 from the companion device 5, in which the user time is used for dose time tracking. Using the system 100, the prescription app 12 can know the time of the dose relative to the current time.

Once the companion device 5 receives the dose related information (e.g., which can include the time information and dose setting and/or dispensing information, and other information about the pen device 10 related to the dosing event), the companion device 5 stores the dose related information in memory, e.g., which can include among a list of doses or dosing events. In some implementations, for example, via the user interface of the prescription app 12, the companion device 5 allows the patient to browse a list of previous doses, to view an estimate of current medicament active in the patient's body ("medicament on board") based on calculations performed by a medicine calculation module of the prescription app 12, and/or to utilize a dose calculation module of the software application to assist the patient regarding dose setting information on the size of the next dose to be delivered. For example, the patient could enter carbohydrates to be eaten, current blood sugar, and the companion device 5 would already know insulin on board. Using these parameters, a suggested medicine dose (e.g., such as insulin dose), calculated by the dose calculation module, may be determined. In some implementations, for example, the companion device 5 can also allow the patient to manually enter boluses into the pen device 10 or another medicine delivery device. This would be useful if the patient was forced to use a syringe, or if the battery in the pen device 10 was depleted.

Example embodiments and implementations of the disclosed intelligent medicine administering system 100, including the prescription app 12 operable on a companion device able to communicate with a medical device (e.g., medicine injection device such as a pen device), are described. Some examples of features of an intelligent medicine administering system that can be used with the example methods, devices and systems for providing a prescription-regulated software controls on the system are described in U.S. Pat. No. 9,672,328 B2, entitled "Medicine Administering System Including Injection Pen and Companion Device," the entire content of which is incorporated by reference in this patent document.

While the disclosed embodiments described herein are primarily based on diabetes management systems and methods involving insulin pen, prescription app associated with the insulin pen, and/or glucose monitoring devices to facilitate understanding of the underlying concepts, it is understood that the disclosed embodiments can also include treatment of other health conditions using other medications by the pen device, prescription app, and/or monitoring of other analytes by sensor devices.

Figure 2:
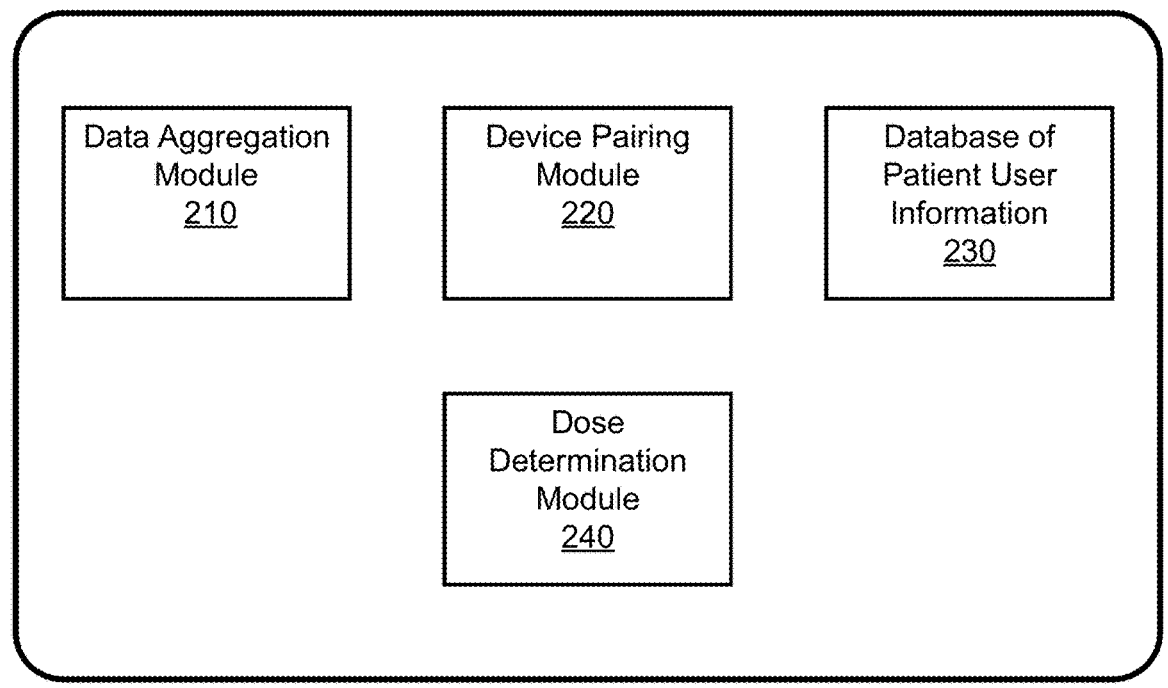
FIG. 2 shows a block diagram of an example software architecture of data processing modules in accordance with some embodiments of the prescription app of the intelligent medicine administrating system of FIG. 1A.

FIG. 2 shows a block diagram of a software architecture of data processing modules 200 in accordance with some example embodiments of the prescription app 12 of the intelligent medicine administrating system 100. In some embodiments, some or all of the data processing modules of the software architecture of the prescription app 12 are resident on the companion device 5. In some implementations of the example software architecture 200, the modules operate to control certain functionalities of the companion device 5, which includes aggregating and processing output signals transmitted by the medical injection device (e.g., pen device 10) to execute a device pairing for validation of the medicine injection device and unlocking of some or all functionality of the prescription app 12 on the companion device 5.

In some embodiments of the software architecture 200, some or all of the data processing modules are resident on the companion device 5, e.g., resident in the data processing unit. In some embodiments of the software architecture 200 of the system 100, some of the data processing modules can be resident on the pen device 10, e.g., resident in the electronics unit. The data processing modules of the prescription app 12 on the companion device 5 may be include different or the same data processing modules of the software architecture 200 resident on the pen device 10. For example, one of the data processing modules that can be resident on and implemented by the pen device 10 includes a device pairing module 220 to receive and process the output signals from the pen device 10 to pair with the prescription app 12 resident on the companion device 5. Similarly, in some embodiments, for example, some of the data processing modules of the software architecture 200 can be embodied as part of a data processing system in the cloud (e.g., resident on one or more cloud computers).

In some implementations, the pen device 10 can be paired to the companion device 5 to enable some or all protected features of the prescription app 12 associated with a regulated use of the pen device 10 and/or data management on the companion device 5 which require a medical prescription for use by the patient user. The secure pairing methods ensure that the prescription app 12 resident on the companion device 5 is specifically associated with a particular pen device 10 belonging to the patient user, e.g., who has a prescription corresponding to use of some or all features of the prescription app 12.

In some example embodiments, a method for secure unlocking and enablement of a prescription software application (e.g., prescription app 12 of the system 100) includes providing the prescription app 12 to the companion device 5 through download or other to load the prescription app 12 on the companion device 5. For example, due to the secure enablement of the prescription app 12, the prescription app 12 can be available for download on a third-party server such as an app store by a device maker or other party. The downloaded prescription app 12 is disabled from full or partial use to prevent a user from accessing certain functionality of the application, e.g., such as features subject to regulation that could cause misuse or patient harm without a proper prescription to the app. The method includes conducting a prescription app-device pairing process to unlock and/or enable certain features of the prescription app 12, which includes transmitting, by the pen device 10, a wireless signal (e.g., via BLE, NFC, etc.) to be received by the companion device 5, in which the companion device 5 processes the received wireless signal to identify and/or authenticate the pen device 10 to allow the pairing (bonding) of the devices and enabling of the prescription app 12 (e.g., unlocking of some or all of the features of the app).

In some implementations of the prescription app-device pairing process, for example, the prescription app 12 polls the data processing unit of the companion device 5 to verify that a device associated with the app, i.e., the injection pen device 10 to be associated with the prescription app 12, has been identified and/or authenticated by the companion device 5. For example, the polling is performed when the prescription app 12 is initially opened and/or opened without yet being unlocked or enabled.

In some implementations, for example, the prescription app-device pairing process includes the pen device 10 providing a security code within the transmitted wireless signal that is receivable on the companion device 5. When the prescription app 12 is opened for the first time, the features of the prescription app 12 are disabled by default and can, through this automated process, be unlocked and enabled when the transmitted security code is processed by the device pairing module 220 of the prescription app 12. For example, the prescription app 12 may initially only display, on the companion device 5, a default screen (e.g., one or a group of display screens) informing the user that the prescription app 12 is checking for the security code ("prescription code") to be transmitted by the associated pen device 10 of the user. In some implementations, the displayed default screen can include an indicator that pairing is undergoing, a list of trouble-shooting steps should pairing be impaired or unsuccessful, and/or contact information to seek assistance with the prescription app-device pairing process.

In some implementations, the prescription app-device pairing process can generate a unique security code that only corresponds to the patient user. For example, when the pen device 10 is initially operated by its intended patient user (i.e., the patient user that purchases the specific pen device 10 using a prescription given to him/her by his/her prescribing physician or nurse practitioner), the pen device 10 sends a device identification code to a server and/or database computer of the data processing system 120 that indicates that the particular pen device 10 is now eligible for use with the prescription app 12. The system 100 stores the device identification code, which can be accessed by the prescription app 12 (via communications from the companion device 5) during the prescription app-device pairing process to validate the security code received by the companion device 5 directly from the pen device 10 with the device identification code stored in the database. If matched, the prescription app 12 is enabled and unlocks the prescription-regulated features of the app.

In some embodiments of the software architecture 200 for the prescription app 12, the data processing modules may also be configured to process health metric data and contextual data obtained by the prescription app 12 on the companion device 5, from the pen device 10, from the sensor device 50, and/or from other devices of the patient user and/or apps on the companion device 5. In some embodiments, for example, the software architecture 200 includes a data aggregation module 210 to obtain the health metric data from a device, such as the pen device 10, sensor device 50, and/or other devices or apps in communication with the companion device 5. The software architecture 200 includes or is in communication with a database 230 to store the health data and contextual data associated with the patient user and populations of patient users. In various embodiments, the database 230 can be resident on the data processing system 120, e.g., in the cloud. In some embodiments, the software architecture 200 includes a dose determination module 240, such as a dose calculator module, to autonomously calculate a dose of the medicine associated with dose injections from the pen device 10 based on time-relevant and context or circumstances-relevant data specific to the patient user of the pen device 10. The example modules shown in the software architecture diagram can be organized to provide data to one another in various ways, including directly (e.g., module-to-module) and/or indirectly (e.g., via an intermediary module), based on a periodic, an intermittent, and/or a per-request basis.

Figure 3A:
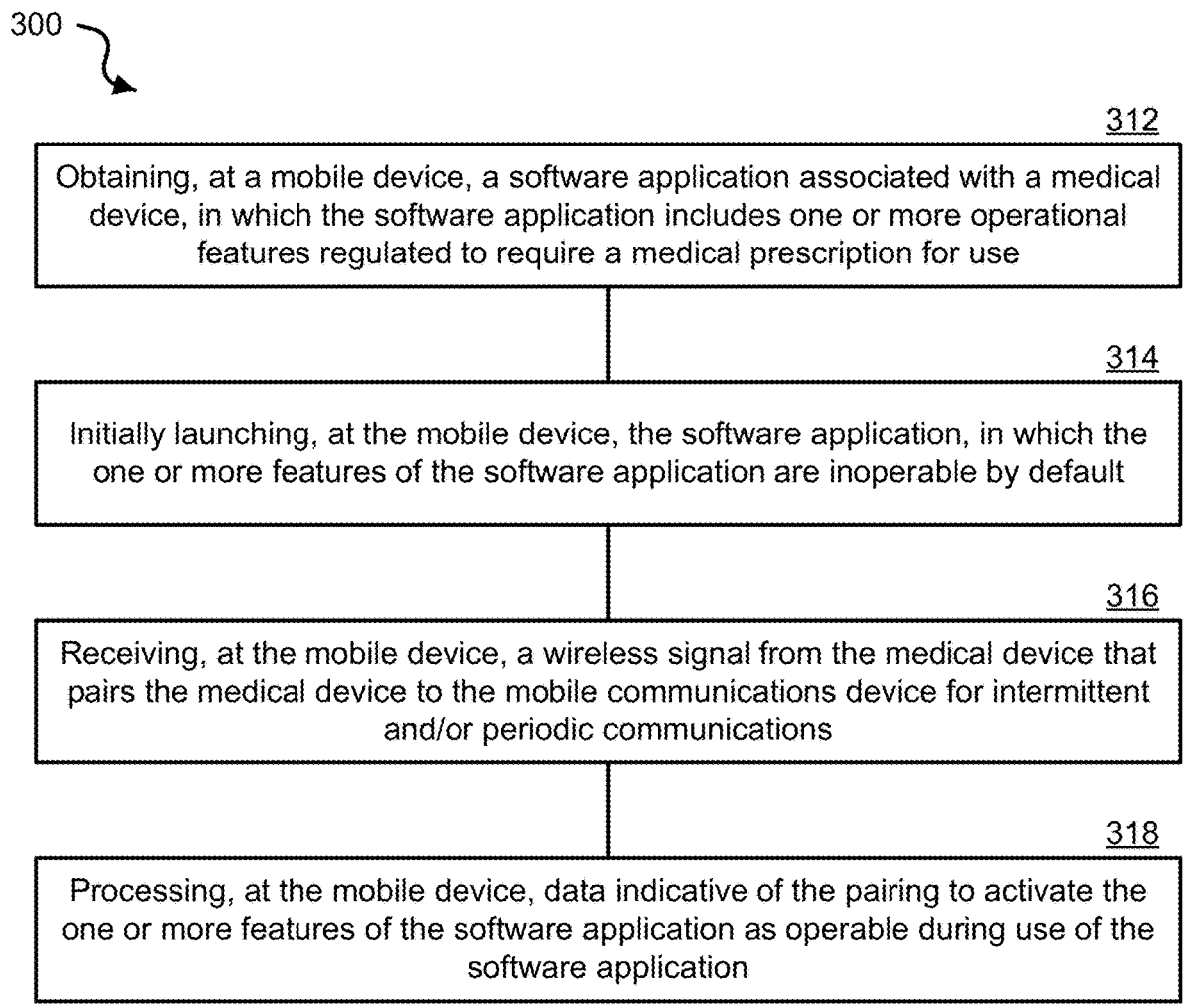

FIG. 3A shows a diagram of an example embodiment of a method 300 for providing a medically-prescribed software application. The method 300 includes a process 312 to obtain, at a mobile device (e.g., companion device 5), a software application associated with a medical device (e.g., pen device 10), in which the software application (e.g., prescription app 12) includes one or more operational features regulated to require a medical prescription for use. For example, when these one or more operational features of the software application are executed, it causes the mobile to device to operate in a manner that is regulated (e.g., by the U.S. FDA) to require a prescription for use of the software application. The method 300 includes a process 314 to initially launch, at the mobile device, the software application, in which the one or more features of the software application are inoperable by default. The method 300 includes a process 316 to receive, at the mobile device, a wireless signal (e.g., BLE, NFC, etc.) from the medical device that pairs the medical device to the mobile device for intermittent and/or periodic communications. The method 300 includes a process 318 to process, at the mobile device, data indicative of the pairing to activate the one or more features of the software application as operable during use of the software application. In some implementations of the process 318, the processing of the data indicative of the pairing includes activating, at the mobile device, the one or more operational features of the software application as operable by using data received during pairing of the medical device with the mobile device.

Figure 3B:
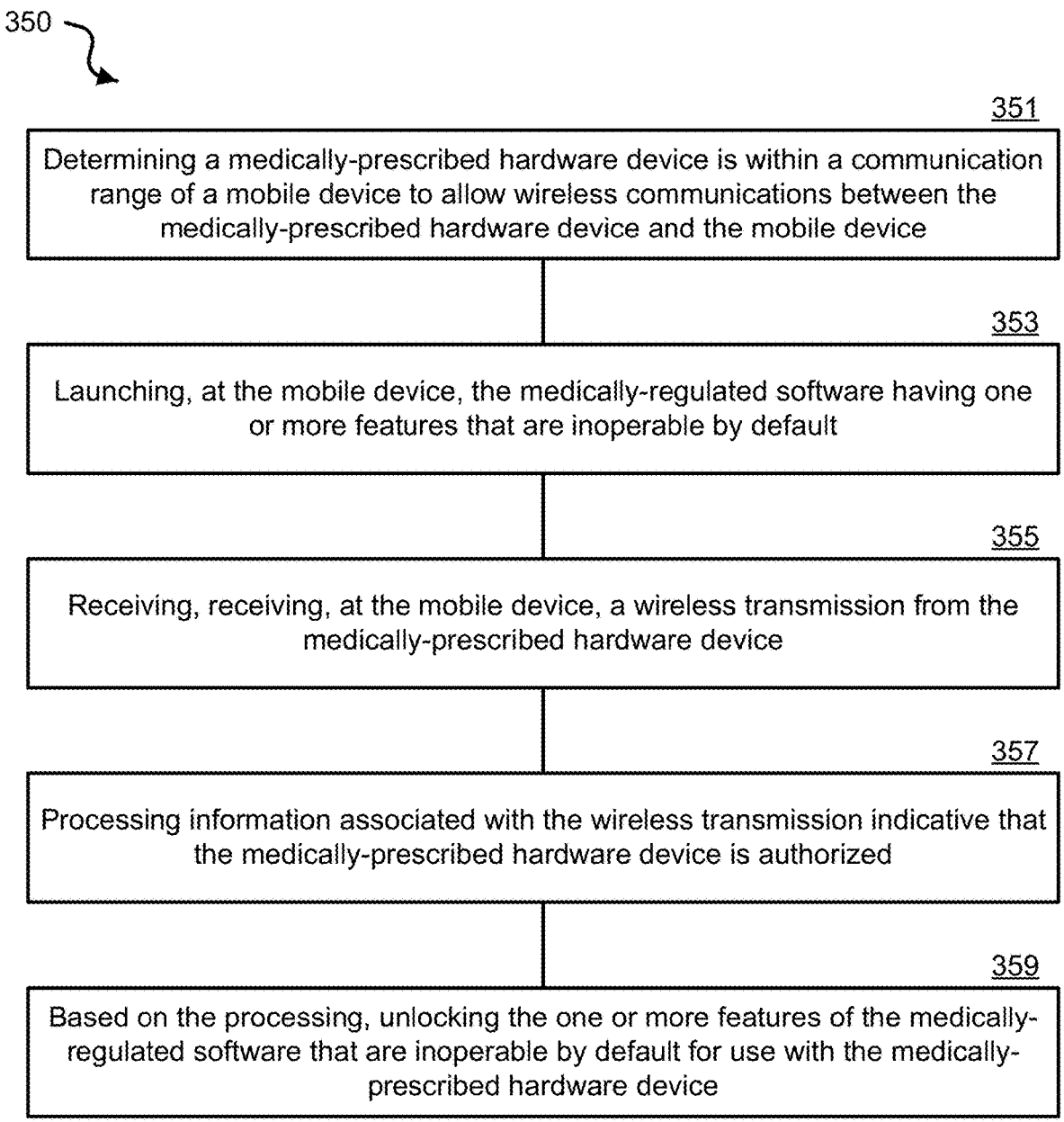

FIG. 3B shows a diagram of an example embodiment of a method 350 for enabling use of a medically-regulated software (e.g., prescription app 12) on a mobile device (e.g., companion device 5) with a medically-prescribed hardware device, e.g., such as a medicine injection device like the pen device 10. The method 350 includes a process 351 to determine that the medically-prescribed hardware device is within a communication range of the mobile device having the medically-regulated software so as to allow wireless communications between the medically-prescribed hardware device and the mobile device. The medically-regulated software application has one or more features that are inoperable by default, and these one or more features, when executed, cause the mobile device to operate in a manner that is regulated to require a medical prescription for use of the medically-regulated software application. The method 350 includes a process 353 to launch, at the mobile device, the medically-regulated software having the one or more features that are inoperable by default. The method 350 includes a process 355 to receive, at the mobile device, a wireless transmission from the medically-prescribed hardware device. The method 350 includes a process 357 to process information associated with the wireless transmission indicative that the medically-prescribed hardware device is authorized. The method 350 includes a process 359 to unlock the one or more features of the medically-regulated software that are inoperable by default for use with the medically-prescribed hardware device when the process 357 has determined the medically-prescribed hardware device is authorized.

FIG. 3C shows a diagram of an example embodiment of a method 370 for enabling use of a medically-regulated software (e.g., prescription app 12) on a mobile device (e.g., companion device 5) with a medically-prescribed hardware device, e.g., such as a medicine injection device like the pen device 10. The method 370 includes a process 371 to determine that the medically-prescribed hardware device is within a communication range of the mobile device having the medically-regulated software so as to allow wireless communications between the medically-prescribed hardware device and the mobile device. The medically-regulated software application has one or more features that are inoperable by default, and these one or more features, when executed, cause the mobile device to operate in a manner that is regulated to require a medical prescription for use of the medically-regulated software application. The method 370 includes a process 373 to store a code in a memory of the medically-prescribed injection device. The method 370 includes a process 375 to transmit a wireless transmission including the code by the medically-prescribed injection device to the mobile device. The method 370 includes a process 377 to receive, at the medically-prescribed injection device, a subsequent wireless transmission from the mobile device that includes an instruction to carry out a medically-regulated operation of the medically-prescribed injection device, wherein the instruction is transmitted by the mobile device as a result of a validation of the code by the mobile device to authorize unlocking of the one or more features of the medically-regulated software application that are otherwise inoperable by default for use with the medically-prescribed injection device.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method for providing a medically-prescribed software application, comprising:
   obtaining, at a mobile device, a software application associated with a medical device, wherein the software application includes one or more prescription-regulated operational features that, when executed, cause the mobile device to operate in a manner that is regulated to require a medical prescription for use of the software application;
   initially launching, at the mobile device, the software application, wherein the one or more prescription-regulated operational features of the software application are inoperable by default;
   receiving, at the mobile device, a wireless signal from the medical device to pair the medical device to the mobile device for intermittent and/or periodic communications;
   receiving, at the mobile device during pairing of the medical device with the mobile device, prescription data stored on the medical device, the prescription data configured to enable as operable the prescription-regulated operational features of the software application; and
   enabling, at the mobile device, the one or more prescription-regulated operational features of the software application as operable using the prescription data received at the mobile device from the medical device during pairing of the medical device with the mobile device.

2. The method of claim 1, wherein the received wireless signal includes a security code, and wherein the method comprises storing the security code in a memory of mobile device.

3. The method of claim 2, wherein the security code is a unique security code that only corresponds to a patient user who has been prescribed the medical device.

4. The method of claim 2, comprising:
    transmitting, by the mobile device, the security code to a remote server to validate the security code; and
    receiving, by the mobile device, validation data from the remote server to authorize activation of the one or more prescription-regulated operational features of the software application.

5. The method of claim 1, wherein the received wireless signal includes a validation code included in a pairing protocol, and wherein the enabling includes processing the validation code to compare to a predetermined authorization code contained within the obtained software application.

6. The method of claim 1, wherein the medical device includes a medicine injection pen and/or medicine injection pump.

7. The method of claim 1, wherein the mobile device is implemented on a smartphone, a tablet, and/or a wearable device.

8. The method of claim 1, wherein the software application is operable on the mobile device to cause the mobile device to display a default screen prior to enabling as operable the one or more prescription-regulated operational features.

9. The method of claim 8, wherein the default screen includes one or more of an indicator that the pairing is undergoing, a list of trouble-shooting steps should the pairing be impaired or unsuccessful, or a contact information for a user to seek assistance with the pairing process.

10. The method of claim 1, wherein the wireless signal is received using a Bluetooth, Bluetooth Low Energy (BLE), and/or Near Field Communication (NFC) protocol.

11. A method for enabling use of a medically-regulated software application for a mobile device with a medically-prescribed injection device, the method comprising:
    determining that the medically-prescribed injection device is within a communication range of the mobile device so as to allow wireless communications between the medically-prescribed injection device and the mobile device;
    at the mobile device, launching the medically-regulated software application having one or more prescription-regulated operational features that are inoperable by default, wherein the one or more prescription-regulated operational features, when executed, cause the mobile device to operate in a manner that is regulated to require a medical prescription for use of the medically-regulated software application;
    at the mobile device, receiving a wireless transmission from the medically-prescribed injection device to pair the medically-prescribed injection device with the mobile device;
    receiving, at the mobile device during pairing of the medically-prescribed injection device with the mobile device, prescription data stored on the medically-prescribed injection device, the prescription data indicative that the medically-prescribed injection device is authorized; and
    using the prescription data received from the medically-prescribed injection device to enable as operable the one or more prescription-regulated operational features of the medically-regulated software application that are inoperable by default for use with the medically-prescribed injection device.

12. The method of claim 11, wherein the medically-prescribed injection device includes a medicine injection pen and/or medicine injection pump.

13. The method of claim 11, wherein the mobile device is implemented on a smartphone, a tablet, and/or a wearable device.

14. The method of claim 11, wherein the medically-regulated software application is operable on the mobile device to cause the mobile device to display a default screen prior to enabling as operable the one or more prescription-regulated operational features.

15. The method of claim 14, wherein the default screen includes one or more of an indicator that the pairing is undergoing, a list of trouble-shooting steps should the pairing be impaired or unsuccessful, or a contact information for a user to seek assistance with the pairing process.

16. The method of claim 11, wherein the wireless transmission includes a signal in accordance with a Bluetooth, Bluetooth Low Energy (BLE), and/or Near Field Communication (NFC) protocol.

17. A method for enabling use of a medically-regulated software application for a mobile device with a medically-prescribed injection device, the method comprising:
    determining that the medically-prescribed injection device is within a communication range of the mobile device so as to allow wireless communications between the medically-prescribed injection device and the mobile device, wherein the medically-regulated software application is stored on the mobile device and has one or more prescription-regulated operational features that are inoperable by default, and wherein the one or more prescription-regulated operational features, when executed, cause the mobile device to operate in a manner that is regulated to require a medical prescription for use of the medically-regulated software application;
    at the medically-prescribed injection device, storing a prescription code in a memory of the medically-prescribed injection device, the prescription code configured to enable as operable the prescription-regulated operational features of the medically-regulated software application;
    transmitting a wireless transmission including the prescription code from the medically-prescribed injection device to the mobile device during a pairing of the medically-prescribed injection device with the mobile device; and
    at the medically-prescribed injection device, receiving a subsequent wireless transmission from the mobile device that includes an instruction to carry out a medically-regulated operation of the medically-prescribed injection device, wherein the instruction is transmitted by the mobile device as a result of a validation of the prescription code by the mobile device to enable as operable the one or more prescription-regulated operational features of the medically-regulated software application that are otherwise inoperable by default for use with the medically-prescribed injection device.

18. The method of claim 17, wherein the medically-prescribed injection device includes a medicine injection pen and/or medicine injection pump.

19. The method of claim 17, wherein the mobile device is implemented on a smartphone, a tablet, and/or a wearable device.

20. The method of claim 17, wherein the wireless transmission includes a signal in accordance with a Bluetooth, Bluetooth Low Energy (BLE), and/or Near Field Communication (NFC) protocol.

* * * * *